United States Patent
Kolari et al.

(10) Patent No.: US 7,829,305 B2
(45) Date of Patent: Nov. 9, 2010

(54) METHOD FOR MONITORING THE PRESENCE OF BIOFILMFORMING MICROORGANISMS IN PAPER INDUSTRY

(75) Inventors: Marko Kolari, Vantaa (FI); Mirja Salkinoja-Salonen, Helsinki (FI); Terhi Johanna Hatunen, Vaasa (FI)

(73) Assignee: Kemira Oyj, Helsinki (FI)

( * ) Notice: Subject to any disclaimer, the term of this patent is extended or adjusted under 35 U.S.C. 154(b) by 895 days.

(21) Appl. No.: 10/578,324

(22) PCT Filed: Nov. 5, 2004

(86) PCT No.: PCT/FI2004/000654

§ 371 (c)(1),
(2), (4) Date: Dec. 29, 2006

(87) PCT Pub. No.: WO2005/045132

PCT Pub. Date: May 19, 2005

(65) Prior Publication Data

US 2007/0134649 A1    Jun. 14, 2007

(30) Foreign Application Priority Data

Nov. 6, 2003  (FI) ................................. 20031614

(51) Int. Cl.
   *C12Q 1/18*   (2006.01)
(52) U.S. Cl. .............................. 435/32; 435/29; 435/30
(58) Field of Classification Search ........................ None
See application file for complete search history.

(56) References Cited

U.S. PATENT DOCUMENTS

| | | | |
|---|---|---|---|
| 4,912,332 A | 3/1990 | Siebel et al. |
| 5,049,492 A | 9/1991 | Sauer et al. |
| 5,349,874 A | 9/1994 | Schapira et al. |
| 6,361,963 B1 | 3/2002 | Smith et al. |
| 6,410,256 B1 | 6/2002 | Ceri et al. |
| 6,599,696 B2 | 7/2003 | Olson et al. |
| 2001/0049975 A1 | 12/2001 | Ceri et al. |
| 2003/0012688 A1 | 1/2003 | Kippenhan, Jr. |
| 2003/0155090 A1 | 8/2003 | Holmberg et al. |
| 2006/0120916 A1 | 6/2006 | Kolari et al. |

FOREIGN PATENT DOCUMENTS

| | | |
|---|---|---|
| EP | 0 505 023 A1 | 9/1992 |
| EP | 0 755 436 B1 | 1/1997 |
| EP | 0 327 386 B1 | 8/1998 |
| EP | 1 118 859 A2 | 7/2001 |
| EP | 1 350 431 A1 | 10/2003 |
| FI | 95597 C | 10/1995 |
| FI | 116030 B | 9/2005 |
| FI | 115502 B | 5/2006 |
| WO | WO-99/06589 A1 | 2/1999 |
| WO | WO 02/10434 A2 | 2/2002 |
| WO | WO-02/088298 A1 | 11/2002 |
| WO | WO-2004040982 A1 | 5/2004 |

OTHER PUBLICATIONS

Kolari, M. et al.; Journal of Industrial Microbiology & Biotechnology, (2003) 30; pp. 225-238.

*Primary Examiner*—Jon P Weber
*Assistant Examiner*—Satyendra K Singh
(74) *Attorney, Agent, or Firm*—Birch, Stewart, Kolasch & Birch, LLP

(57) ABSTRACT

The invention is directed to a method for detecting the presence of biofilm-forming microorganisms in a paper or board making process for determining the need of an anti-biofilm agent in the process. The method comprises the steps: (a) subjecting a sampler device in the process line for a period of time to enable said microorganisms to form a biofilm in situ in said process on the surface of the sampler, (b) optionally treating said formed biofilm in a solution of a test anti-biofilm agent for a period of time, then (c) contacting said biofilm with a liquid growth medium in a recession of a culturing device for a period of time, and (d) removing the growth solution from the recession of said device and detecting qualitatively and/or quantitatively the presence or absence of a biofilm adhered on the walls of the recession. An assembly kit is also provided.

12 Claims, 1 Drawing Sheet

US 7,829,305 B2

Figure 1:
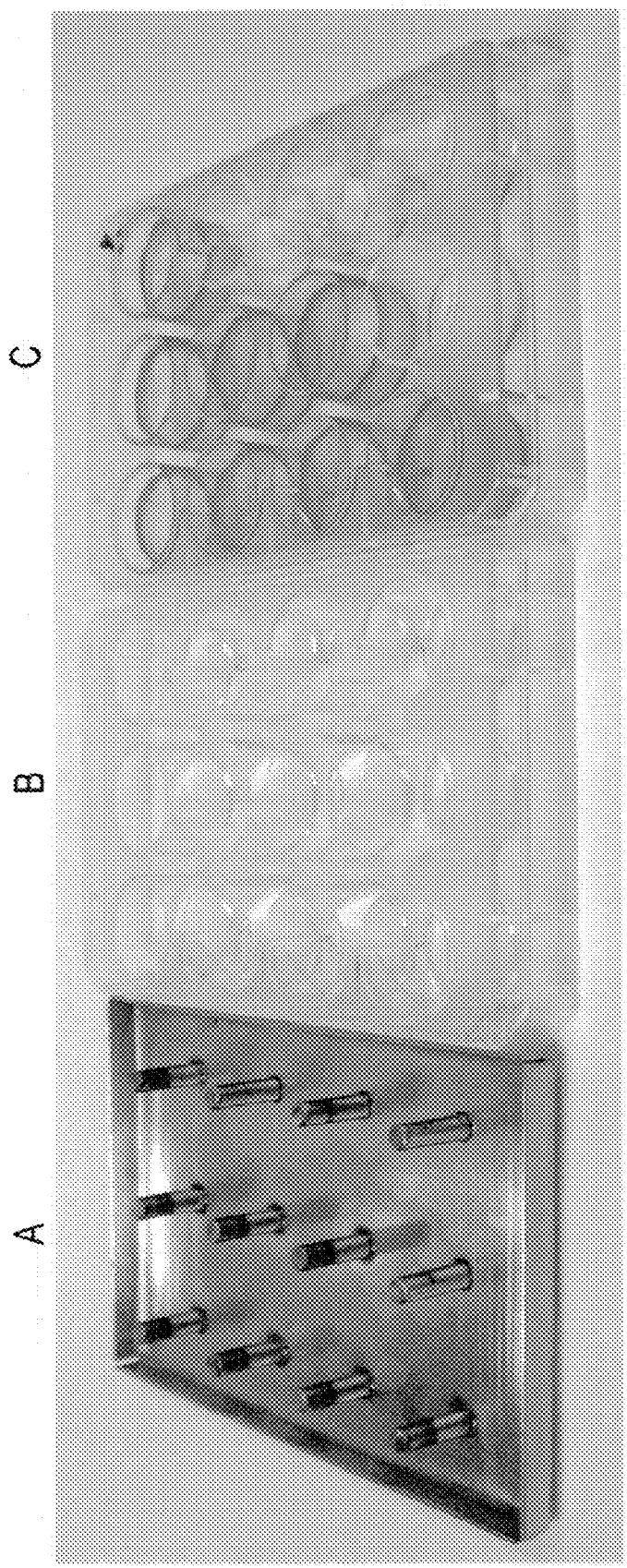

METHOD FOR MONITORING THE PRESENCE OF BIOFILMFORMING MICROORGANISMS IN PAPER INDUSTRY

FIELD OF THE INVENTION

The present invention relates to a method for monitoring the presence of biofilm-forming microorganisms in paper and board making industry for determining the need of an anti-biofilm agent in the process. Furthermore an assembly kit for the method is also provided.

BACKGROUND OF THE INVENTION

The paper and board making processes contain warm process waters (e.g. 45-60° C.) that are rich in biodegradable nutrients and have a beneficial pH (e.g. pH 4-9) thus providing a good environment for the growth of microorganisms. The microbes in the process show biofilm-forming, i.e. surface-attached, growth and free-swimming, i.e. planktonic, growth. Several problems in the paper industry are caused by the biofilms, i.e. slime layers, which develop on the surfaces of the process equipments and can rip off from the surfaces. Biofouling of the machine surfaces and the loose biofilm/agglomerates can cause severe process disturbances: reduce water flow; block filters, wires, etc.; deteriorate the end-product quality, e.g. by causing holes or colored spots in the end product; or break the whole paper web. The biofilms are difficult to remove from the surfaces of the process equipment and often require the use of very strong chemicals.

For controlling the microbe growth e.g. biocides have been added to the process waters. Planktonic microbes have been efficiently controlled by the biocides; however, the use of biocides has not solved all biofilm problems in the paper or board machines. Several reasons exist for that, e.g. a wide variety of microbes are growing in the papermaking process and it is now also known that bacteria growing in a biofilm are generally more resistant to biocides than the planktonic microbes.

One of the present inventors, Kolari, M. has recently investigated the biofilm-formers in paper and board industry in Attachment Mechanisms and Properties of Bacterial Biofilms on Non-Living Surfaces, Dissertationes Biocentri Viikki Universitatis Helsingiensis 12/2003, Ph.D. thesis, University of Helsinki, Finland. In the study biofilm-formers were identified and their interactions investigated. Accordingly, the processes were found to comprise different types of biofilm-forming microorganisms: primary biofilm-formers that are capable of adhering to clean surfaces and secondary biofilm-formers which then adhere to the primary biofilms. The primary biofilm-formers seem to be a prerequisite for successful surface colonization of several other microbes in paper and board machines. E.g. *Deinococcus geothermalis* is a primary biofilm-former and strains of several *Bacillus* species adhere to the primary biofilms of this bacterium. Kolari, M. et al in Journal of Industrial Microbiology & Biotechnology (2003) 30, p. 225-238, describe more primary biofilm-forming bacteria. Amended with the newest, unpublished data, the relevant primary biofilm-forming microorganisms recognized thus far are: species *Deinococcus geothermalis*; genus *Meiothermus*, such as species *M. silvanus* or *M. ruber*, genus *Azospirillum*; genus *Burkholderia*, such as *B. multivorans* or *B. cepacia*; genus *Porphyrobacter*, such as *P. cryptus*; genus "*Rubellimicrobium*"; and genus *Thermomonas*, such as *T. haemolytica* or *T. hydrothermalis*. The primary biofilm-formers are typically moderately thermophilic, some with maximum growth temperatures as high as 67° C., and most of the strains showing the fastest growth at temperatures of 45 to 55° C. To overcome the problem with the biofilms in paper industry was, however, not discussed.

As stated above, in the context of slime formation in paper and board machines, it appears that the biofilm-formers are the most harmful microbes and their prevention would improve the functioning of the process machines and thus productivity of the process. For that purpose the present applicant has disclosed in the recent patent applications of FI 20021986 and FI 20021987 a new type of anti-biofilm agents, which are of a plant origin and can be used for the prevention of the formation of the biofilm and/or for removal of the already formed biofilm in a paper or board making process.

The efficient use of the biocides or said anti-biofilm agents would require an effective monitoring method. In paper industry, the typical monitoring method for the microbe growth is the cultivation of a sample of process water in laboratory. Such cultivation methods are, however, time-consuming and complicated, i.e. they take several days and require i.a. the use of various growth media for isolation and identification of different types of microbes in a sample. Moreover, it is known that the microbe growth in laboratory is culture-medium-dependent, thus part of the microbes present in a sample are often unable to grow under the laboratory conditions. Furthermore, the monitoring is typically focused on the free-swimming microbes. Efficient methods for monitoring the effects of anti-biofilm agents on the biofilm-forming microbes have been lacking. Therefore, e.g. biocides are conventionally used for non-selective inhibition of all microbes in the process, whereby high amounts of biocides are often required.

FI 95597 of the present applicant describes a device which can be used in laboratory or be brought in the paper process for producing a biofilm on the slides thereof. The biofilm is formed with pure yeast cultures or by placing the device into the process waters. The growth is analyzed by counting the number of yeast cells per $cm^2$ using conventional plating methods. As already mentioned the plating method is time-consuming both for identifying the harmful microbes and for screening of e.g. a suitable biocide. Moreover, a part of the microbes in the biofilm may fail to grow on the culture medium.

U.S. Pat. Nos. 6,326,190 and 6,410,256 describe a method, wherein a bacterial biofilm is formed on a surface of a plurality of protrusions arranged in a device and the sensitivity of the biofilm to antibacterial agents are determined. However, in said methods the biofilm has been formed with the conventional time-consuming technique, i.e. by using pure cultures which are cultivated in laboratory, in a specific laboratory device.

Accordingly, there exists a need in the paper industry for more effective methods for monitoring the slime formation.

OBJECT OF THE INVENTION

The object of the present invention is to provide a further detection method for the paper industry that enables an efficient and timesaving means for monitoring the microbiological state in a paper or board making process.

A further object of the invention is to provide a detection method, which can be used for selective monitoring of biofilm-forming microbes that are harmful in the paper industry, and which can be used for screening for the anti-biofilm agent that is the most active towards biofilms grown under the process conditions.

Another object of the invention is to provide an assembly kit, which is very feasible for the detection method of the invention to be carried out at the process site.

SHORT DESCRIPTION OF THE DRAWINGS

FIG. 1 represents one preferable embodiment of the sampler device and treatment/culturing device of the invention used in the example. FIG. 1A shows an array of samplers as protrusions. FIG. 1B shows an array of recessions in the culture device. FIG. 1C shows that several of the recessions in the culture device show growth prevention of biofilm.

DETAILED DESCRIPTION OF THE INVENTION

The inventors have now found that a biofilm can be formed in situ in the paper or board making process on a surface of a sampler device and the biofilm formed thereon can be analyzed, if desired, directly from said surface for the presence and the quantity of the harmful biofilm-formers, especially of the primary biofilm-formers. Thus in the present invention the in situ formed biofilm needs not to be removed from the sampler surface.

Moreover, the inventors have developed a detection method for the biofilm formed on the surface of the sampler, which is faster than the cultivation-based methods in current use and which can be used for detecting the occurrence of the actual biofilm-formers at the particular process site, and for the selection of the most efficient anti-biofilm agent and an effective concentration thereof against said actual biofilm at that site.

The detection method now developed can be used for monitoring the need of an anti-biofilm agent in a paper or board making process, i.a. whether any anti-biofilm agent is needed, a further addition thereof is needed and/or the effective/optimum amounts of the anti-biofilm agent to be added.

The characterizing features of the invention are defined in the claims below.

Accordingly, the invention provides a detection method for monitoring the microbe growth in a paper or board making process for determining the need of an anti-biofilm agent in the process, the method comprising the steps of:

(a) subjecting a sampler device in the process line for a period of time, e.g. for 3 h to 7 d, preferably for 12 h to 3 d, to enable said microorganisms to form a biofilm in situ in said process on the surface of the sampler, (b) optionally treating said formed biofilm, preferably the surface of the sampler with said formed biofilm thereon, in a solution of a test anti-biofilm agent for a period of time, e.g. 10 minutes to 4 hours, preferably for 1-2 h, at the temperature between the ambient temperature and 65° C., e.g. at 35-65° C., preferably at 40-60° C., more preferably close to the temperature of the sampling site of the process line, such as at 40-60° C. then (c) contacting said biofilm, preferably the surface of the sampler with said biofilm thereon, with a liquid growth medium in a recession of a culturing device for a period of time, e.g. for 8-48 h, preferably for 8-24 h, more preferably for 16 to 20 h, at the temperature between the ambient temperature and 65° C., e.g. at 35-65° C., preferably at 40-60° C., more preferably close to the process temperature of the sampling site of the process line, such as at 40-60° C., (d) removing the growth solution and, in case the biofilm is in place on the surface of the sampler, also the sampler from the recession of said device and detecting qualitatively and/or quantitatively the presence or absence of a biofilm adhered on the walls of the recession.

As to the used terms, "Paper or board making process" and "process line" as used herein covers the process lines of wet manufacturing processes for raw materials of paper and pulp industry, pulping process, the pulp drying process, the actual paper or board making process and the equipment thereof including the paper and board machines. The paper and board machines are understood to comprise both the wet-end with wire section and the drying section.

The sampler device can be placed in any place of the process lines, including the wet-end part of the paper or board machines and the dry end of the process lines. Furthermore the exposure environment of the sampler device can be any process media including process waters, pulp suspensions, circulating and wastewaters, raw materials, reagents, and intermediate products etc. The device can be immersed in the liquid streams or brought in the splash area of the process line.

Moreover, the sampler device may comprise means for fixing it e.g. on the surface of the paper making equipment, e.g. in a process water container of a paper machine. Alternatively, the sampling sites of the process line may be provided with a mounting means, wherein the sampler device can be fixed for the period of biofilm formation on the surface thereof. The time required for forming the biofilm on the surface of the device in the process depends on the site in the process line and on the process type, and can be chosen by a skilled person accordingly. E.g. when the device is in the wire section of a neutral paper machine the exposure time is 12 to 48 h depending on the cleanliness of the machine, i.e. delay from the last standstill and washing.

After the removal of the sampler from the process, the surface exposed to biofilm formation may optionally be rinsed or washed to remove any loose material.

In a preferred embodiment of the invention the formed biofilm is subjected on the optional treatment step (b) and the culturing step (c) while being in place, i.e. adhered, on the surface of the sampler.

Preferably, the method comprises the treatment step (b) with one or more test anti-biofilm agents for the selection of the most efficient anti-biofilm agent at an advantageous concentration.

The treatment step (b) is effected preferably by immersing the surface of the sampler with the biofilm thereon in a solution which contains the test anti-biofilm agent. The treatment can be effected in a treatment device provided with a recession which is filled with a solution comprising the test anti-biofilm agent. The test anti-biofilm agent is dissolved in the solution which is preferably a liquid growth medium, sterilized water and/or process water. The treatment is preferably effected by shaking the treatment device in a conventional shaker, e.g. between 150-250 rpm, for a period of time and at a temperature as e.g. defined above. After the treatment step the surface is suitably washed e.g. with sterile water. Preferably, a reference sample is also provided from the same sampling site, which is treated with same solution but in the absence of any test anti-biofilm agent.

In the present method, preferably one or more test anti-biofilm agents are tested at various concentrations for their efficiency against the biofilm-formers present in the monitored process and for determining the useful/optimal concentration of the agent to be used at that process site. In case of several anti-biofilm agents/concentrations several sampler devices can be used, which have been kept in the same site of the process line, each sampler for one agent and for one concentration. More preferably, the sampler device is provided with plurality of separate surfaces, whereby each separate surface can be treated in step (b) with one anti-biofilm agent and one concentration, and also cultured separately in step (c). Furthermore, in step (b) one or more of the devices or surfaces are typically left untreated with the test anti-biofilm agent, as a reference samples, i.e. treated with mere solution. The treatment step (b) of the invention provides reliable information on the efficiency of the tested anti-biofilm agents against the harmful biofilms in the process, since the test is focused against the true biofilm-formers in their biofilm-mode of growth, i.e. in the pre-grown biofilm.

After the optional treatment step (b) the treated biofilms may be rinsed or washed before the culturing step (c). The culturing of the optionally treated biofilms is carried out in a culturing device provided with a recession which is filled with a liquid growth medium, preferably by immersing said surface of the sampler with the optionally treated biofilm thereon in said solution. The time and temperature used in the culturing step is e.g. as defined above. In a preferred embodiment the culturing step is effected with shaking e.g. with a conventional shaker, e.g. at 150-260 rpm, since the shaking has been found to be very beneficial for the biofilm-formation. The shaker may suitably be arranged with a heating means for providing the desired temperature. Step (c) is used for forming a biofilm on the walls of the device, which can then be stained in the subsequent step (d) to detect qualitatively and/or quantitatively the presence or absence of the biofilm-formers in the sampling site of the process line. Preferably the method comprises the treatment step (b), whereby this step shows the extent of biofilm-forming microbes that survived through the anti-biofilm agent treatment step.

Accordingly, after the culturing step the growth solution and, in case the biofilm is treated in place, i.e. while adhered on the surface of the sampler, in the optional step (b) and in the following step (c), also the sampler are removed in step (d) from the recession of the culturing device, the recession is optionally washed, preferably with sterile water, to remove any loose material, and any biofilm-forming microorganisms adhered on the walls of the recession are stained, and the presence and/or intensity of the color formation in the recession is detected qualitatively, e.g. visually, or quantitatively, e.g. spectrofotometrically, in a known manner. Suitable staining agent(s) include any conventional agent suitable for staining the biofilms, such as General stains for showing the biomass, such as crystal violet or safranin,
Stains for showing the cell number, such as acridine orange, ethidium bromide, DAPI, SYTO16 or other nucleic acid stains,
Viability stains for the microbe cells, such as LIVE/DEAD™, CTC or various tetratzolium compounds,
Function-specific fluorescent stains, such as fluorescent enzyme substrates for the detection of starch degrading activity, chitinase activity, esterase activity, lipid ester hydrolyzing activity or phosphatase activity.

In a preferred embodiment of the method of the invention the sampler device comprises a plurality of elongated protrusions supported, i.e. connected, on a support, whereby, when brought in the process, the biofilm is formed similarly on each surface of the protrusions. The material of the protrusions may be e.g. stainless steel, plastics, such as polystyrene, or ceramics, preferably stainless steel. In said embodiment the optional treatment device is also provided with a plurality of recessions for said solutions containing one or more test anti-biofilm agents at one or more concentrations, one test anti-biofilm agent and one concentration in each recession, and for said solution without the test anti-biofilm agent (=for the reference), so that the protrusions of said sampler can be immersed in said recessions, one protrusion in each recession, after the sampler is removed from the sampling site of the process line. In said embodiment also the culturing device comprises a plurality of recessions containing the growth solution, so that the protrusions of said sampler, optionally treated in step (b), can be immersed in said solution in the recessions of the culturing device, one protrusion in each recession.

The biofilm formed on the surface of the protrusions is surprisingly sufficient for the method of the invention and has the further benefit that no removal of the biofilm from the protrusions is required which simplifies and accelerates the monitoring. Major benefit of the present easy-to-use embodiment of the invention is that several different anti-biofilm agents can be tested simultaneously against plurality of similar biofilms pre-grown under true process conditions.

Moreover, with the present invention the actual biofilm-formers of a sampling site of the process line can be tested for the anti-biofilm agents in their actual biofilm-growing state, whereby more reliable results can be obtained for the efficiency of the tested anti-biofilm agents.

Said preferred sampler device can be any system wherein the elongated protrusions are fixed from one end on a support, preferably on a planar support. The size of the sampler is not limited and can vary depending on the chosen sampling place in the process and the assaying system. In a further preferred embodiment the sampler device comprises a plurality of pins or pegs arranged in rows and fixed from one end on a support plate; and the treatment device of the optional step (b) and the culturing device of the step (c) are plates provided with a plurality of wells arranged in rows and adapted for receiving one protruding pin or peg in one well so that each pin/peg of the sampler device sits in each well of the plate of the treatment and culturing device. Preferably, sampler devices are lids provided with pin/peg rows fixed permanently thereon, so that the lids can be used together with e.g. commercially available multi-well plates, such as 6-, 12 or 24-well plates, preferably 12-well plates, such as 12-well polystyrene plates, as the treatment device (b) and the culturing device (c). Naturally, it is desirable to choose the number and rows of the wells of the treatment and culturing plates, which match with the number and rows of the pins/pegs of the lid so that, when the lid is placed on the multi-well plate, each pin/peg sits in one well of the plate. Thus during the treatment and culturing step one end of the pins/pegs is immersed in the liquid medium present in the wells of the plate while the other end being fixed on the lid.

The sampler device, e.g. the lid with pins/pegs, has been found to be very beneficial for the production of biofilm in situ in the paper or board making process. And it has also been found that no coverage/casing is needed for the sampler of the invention in the process, but the sampler can be placed and the protrusions exposed as such in the process, so that the protrusions are directly in contact with the process conditions, e.g. to the process water streams or splashes.

The biofilm development by primary biofilm-formers on the sampler device can be detected even within 12 to 48 h. The efficacy of anti-biofilm agents against the pre-grown biofilms can be effected even within 18 hours. Thus the present method enables to react rapidly to any changes in the biofilm growth within the process and also to any problematic situations already occurred due to said microorganism over to the methods of the prior art.

Accordingly, in one preferable embodiment a continuous monitoring is effected in one or more locations of the process, whereby the action required, e.g. need of addition or of a further addition of the anti-biofilm agent, the type and the effective amount thereof, can determined without any undue delays which are evident when prior art methods are used. For the same reasons the addition of anti-biofilm agents can be optimized and e.g. serious breakdowns in the process predicted and thus avoided.

Optionally, the protrusions on the sampler can be used as the starting point for isolation of the primary biofilm-forming microbes. Optionally, also the protrusions on the sampler can be stained and the biofilm grown during exposure to the process conditions can be quantified.

The invention further provides an assembly kit for monitoring the presence of biofilm-forming microorganism in a paper or board making process and for determining the need of an anti-biofilm agent in the process, and optionally for the selection of the most efficient anti-biofilm agent. The assembly kit comprises at least a combination of (i) a sampler device comprising a plurality of elongated protrusions connected to a support for enabling said microorganisms to form a biofilm in situ in said process on the surface of the sampler,
(ii) optionally a treatment device comprising a plate provided with a plurality of recessions arranged to receive one protrusion of the sampler device in each recession thereof,
(iii) a culturing device comprising a plate provided with a plurality of recessions arranged to receive one protrusion of the sampler device in each recession thereof,
(iv) a shaker for shaking the treatment and/or the culturing device,
(v) optionally a detector for detecting the presence or absence of any stained microbes adhered in the recessions of the culturing device, and
(vi) reagents comprising
  (a) one or more test anti-biofilm agents suitable for the paper industry, preferably in one or more dilutions,
  (b) a liquid growth medium,
  (c) staining agent, and
  (d) optionally a washing solution, such as sterile water.

Preferably, assembly kit comprises (i) said sampler which is a lid provided with a plurality of pins or pegs in rows fixed from one end on the lid, (ii) the treatment device and (iii) the culturing device, which both are multi-well plates provided with a plurality of wells in rows, whereby the pins/pegs of the sampler sit in the wells of the treatment and of the culturing plate, one pin/peg in each well, when the sampler lid is placed on the treatment or culturing plate. Such devices are described above.

Furthermore, in one embodiment (ii) the wells of the treatment plate are prefilled with a solution of one or more anti-biofilm agents, at one or more concentrations, in a liquid growth medium or sterilized water, one test anti-biofilm agent in each well, and that at least one well is prefilled with a growth medium or sterilized water alone (reference well), and (iii) the wells of the culturing plate are prefilled with a liquid growth medium, whereby the wells are sealed off with a removable cover, e.g. foil.

"Anti-biofilm agent" as used herein means generally any agent, which inhibits or prevents the growth of a microorganism. The preferred anti-biofilm agent is suitable for the inhibition of the biofilm-mode of growth of biofilm-forming microorganisms occurring in the paper industry, and more preferably the primary biofilm-formers in the paper industry, e.g. *Deinococcus geothermalis* and/or the other primary biofilm-formers mentioned above. Examples of the anti-biofilm agents include the commercially available biocidical chemicals, such as 2,2-dibromo-3-nitrilopropionamide (DBNPA) and methylene bisthiocyanate (MBT), and also the anti-biofilm agents of plant origin, pure compounds and extracts, such as those mentioned in the patent applications FI 20021986 and FI 20021987 mentioned above, preferably phenolic compounds, e.g. octyl gallate and lauryl gallate, betuline and flavonols, e.g. pentahydroxyflavone and trihydroxyflavone. The term "test anti-biofilm agent" as used above means herein one anti-biofilm agent, e.g. a compound, a mixture of two or more anti-biofilm agents, e.g. any combinations of compounds to be tested and used together, or an extract, e.g. plant extract. The test anti-biofilm agent is preferably dissolved in an aqueous solution as described above.

The growth medium is a solution and can be chosen e.g. from commercially available aqueous growth solutions suitable for the microbes, especially biofilm-formers, more particularly for primary biofilm-formers, occurring in the paper industry, such as R2-broth (commercially available e.g. from Difco), and from the sterilized paper or board machine process waters preferably containing added nutrients.

The part or all of the reagents can be in a multi-dose container, e.g. in a bottle, or in a unit dose container, or prefilled in the recessions of said devices as mentioned above.

Suitable staining agent(s) for the assembly kit include any conventional agent suitable for staining the biofilms, such as those mentioned above. Also a reagent, e.g. ethanol, for dissolving the stain from the recessions can be provided, if the assembly kit is for quantitative determinations.

The assembly kit can further comprise e.g. a shaker suitable for shaking the treatment and/or culturing plates, which shaker may preferably be provided with a heating system for incubating the plates e.g. during the treatment and/or culturing step. Also a detector can be included in the assembly kit, such as a multi-well plate reader for absorbance or fluorescence measurements. The detector type depends on the staining method used for the biofilm microbes. Also pipettes can be included into the assembly kit.

EXAMPLE

In this experiment one embodiment of the sampler device of the invention is used to illustrate the method of the invention for determining the effect of several anti-biofilm agents in inactivation of biofilms formed in a paper machine.

In this embodiment the sampler device comprises 12 stainless steel pegs fixed from one end on a stainless steel lid. The lid with the pegs is presented in FIG. 1 together with a treatment plate with 12 wells adapted to receive the pegs when the lid is placed on the plate. Suitably the lid was designed to be complementary with the commercially available 12-well polystyrene plates.

Three sampler lids are immersed in the clear filtrate silo of a neutral fine paper machine and allowed to hang immersed in said filtrate at the temperature of 52° C. of the process water, for 68 h. Then the samplers are removed, rinsed once with sterilized tap water, and each lid is placed on a 12-well treatment plate so that the pegs with biofilms formed in situ in the process on the surface thereof are immersed in the treatment solution within the wells, each peg in one well, while being supported at the one end by the lid.

Each well of a treatment plate contains 3.5 ml of sterilized tap water alone (reference samples) or 3.5 ml of sterilized tap water together with an anti-biofilm agent at a concentration of 1 to 50 ppm (active substance). The maximum volume of the wells is used so that almost the whole length of the pegs will be exposed to the anti-biofilm agents (the treatment solution). The tested anti-biofilm agents are BCDMH (Bromo-chloro-5,5-dimethyl hydantoine), a mixture of 5-chloro-2-methyl-4-isothiazolin-3-one and 2-methyl-4-isothiazolin-3-one, THPS (tetrakis(hydroxy-methyl)phosphomiumsulphate, DBNPA (2,2-dibromo-2-cyanoacetamide), glutar-aldehyde, MBT (methylene-bis(thiocyanate)), BNPD (bromo-2-nitropropan-1,3-diol), all of which are commercially available.

The anti-biofilm treatment step is carried out by incubating the plates with the lid thereon stagnant at 52° C. for 2 h. After the treatment step the lids are removed from the plate and rinsed three times with sterilized tap water and then placed on the 12-well culturing plates, which are similar to the treatment plates, but the wells contain 2.5 ml of sterile R2-broth (Difco). The culturing plates (plate+lid with the pegs immersed in the wells) are shaken at 250 rpm, at 52° C., for 17 h.

Finally, the pegs and growth media are removed from the wells, the wells are rinsed once with tap water and the microbes adhered on the walls of the wells are stained with safranin. The amount of biofilm produced by the microbes that survived alive through the treatment step with anti-biofilm agents is evaluated visually.

Accordingly, in this experiment DBNPA, BCDMH, THPS and glutaraldehyde can kill or remove the biofilm on the pegs so that no new biofilm is formed during the culturing step. However, after the treatment of the biofilm on the pegs with the mixture of isothiazolones, MBT or BNPD, the treated biofilm is still capable to form new biofilm during the culturing step on the surface of the walls of the wells of the culturing device. Prevention of re-growth of new biofilm in the culturing step with lowest concentration of anti-biofilm agent is achieved by 5 ppm of DBNPA.

The invention claimed is:

1. A method for determining the effectiveness of anti-biofilm agents in a paper-making or board-making process line, said process comprising:
   (a) inserting a sampler device in the process line for a period of time to enable microorganisms to form a biofilm in situ on the surface of the sampler,
   (b) treating the surface of the sampler with said formed biofilm thereon in a solution of a test anti-biofilm agent in a treatment device for a period of time, then
   (c) contacting the surface of the sampler with said biofilm thereon with a liquid growth medium in a recession of a culturing device for a period of time, then
   (d) removing the growth medium and the surface of the sampler from the recession of said culturing device and detecting qualitatively and/or quantitatively the presence or absence of biofilm-forming microorganisms adhered on the walls of the recession.

2. The method according to claim 1, wherein, after the biofilm formation in step (a), said surface of the sampler is treated in step (b) with the solution of the test anti-biofilm agent for the selection of the most efficient anti-biofilm agent.

3. The method according to claim 1 or 2, wherein, in step (a) the sampler device is inserted in the process line for a period of 12 hours to 3 days, in step (b) the treatment step is performed with the solution of a test anti-biofilm agent for a period of 10 minutes to 4 hours, between ambient temperature and 65° C., and then in step (c) the culturing step is performed, optionally with shaking, in the liquid growth medium in the recession of the culturing device for a period of for 8-48 hours, at the temperature between the ambient temperature and 65° C.

4. The method of claim 3, wherein the treatment step (b) is performed with the solution of a test anti-biofilm agent for a period of 1 to 2 hours at a temperature of 40 to 60° C.

5. The method of claim 3, wherein the culturing step (c) is performed with shaking in the liquid growth medium in the recession of the culturing device for a period of 8 to 24 hours at a temperature of 40 to 60° C.

6. The method according to claim 1, wherein, in step (b) the treatment is performed in the treatment device provided with a recession which is filled with a solution comprising the test anti-biofilm agent and a liquid growth medium, sterilized water and/or process water by immersing said surface of the sampler in said solution.

7. The method according to claim 1, wherein the step (c) is performed in the culturing device provided with a recession which is filled with the liquid growth medium by immersing said surface of the sampler in said solution.

8. The method according to claim 1, wherein, in step (d) the sampler surface and the growth medium are removed from the recession of the culturing device, the recession is optionally washed and any biofilm-forming microorganisms adhered on the walls of the recession are stained and the presence and/or intensity of the color formation in the recession is detected qualitatively or quantitatively.

9. The method according to claim 1, wherein, in step (a) the sampler device comprises a plurality of elongated protrusions connected to a support, whereby, when inserted into the process line, the biofilm is formed on the surface of the protrusions.

10. The method according to claim 9, wherein, in step (b) the treatment device comprises a plurality of recessions containing a solution comprising one or more test anti-biofilm agents in one or more concentrations, one test anti-biofilm agent at one concentration in each recession, and said solution without any test anti-biofilm agent as a reference, and that the protrusions of said sampler removed from the process line are immersed in said solution in the recessions such that one protrusion is immersed in each recession.

11. The method according to claim 10, wherein, in step (c) the culturing device comprises a plurality of recessions containing the liquid growth medium, and that the protrusions of said sampler, treated in step (b), are immersed in said growth medium in the recessions of the culturing device such that one protrusion is immersed in each recession.

12. The method according to claim 1, wherein the sampler device comprises a plurality of pins or pegs arranged in rows and fixed from one end on a support plate, and the treatment device of step (b) and the culturing device of step (c) are multi-well plates provided with a plurality of wells arranged in rows and adapted for receiving one protruding pin per well so that each pin of the sampler device sits in each well of the plate of the treatment and culturing device.

* * * * *